United States Patent
Ramdas et al.

(10) Patent No.: US 9,710,607 B2
(45) Date of Patent: Jul. 18, 2017

(54) PORTABLE ELECTRONIC THERAPY DEVICE AND THE METHOD THEREOF

(71) Applicant: ITRACE BIOMEDICAL INC., Miami, FL (US)

(72) Inventors: Radhakrishnan Ramdas, Andhra Pradesh (IN); Bhaskara Rao Bandaru, Andhra Pradesh (IN); Krishnamohan Sharma, Andhra Pradesh (IN)

(73) Assignee: ITRACE BIOMEDICAL INC., Milpitas, CA (US)

( * ) Notice: Subject to any disclaimer, the term of this patent is extended or adjusted under 35 U.S.C. 154(b) by 337 days.

(21) Appl. No.: 14/011,273

(22) Filed: Aug. 27, 2013

(65) Prior Publication Data

US 2014/0200487 A1    Jul. 17, 2014

(30) Foreign Application Priority Data

Jan. 15, 2013  (IN) .............................. 199/CHE/2013

(51) Int. Cl.
*G06F 19/00*    (2011.01)
*A61N 7/00*    (2006.01)
(Continued)

(52) U.S. Cl.
CPC .......... *G06F 19/3456* (2013.01); *A61B 5/026* (2013.01); *A61B 5/02055* (2013.01);
(Continued)

(58) Field of Classification Search
CPC ........ A61B 5/6833; A61B 2017/00172; A61B 2018/00791; A61B 2562/0295; A61B 5/6843; A61B 18/203; A61B 18/14; A61B 2018/00005; A61B 2018/00011; A61B 2018/00452; A61B 2018/00476; A61B 2018/00458; A61M 37/0092; A61N 5/0625; A61N 7/00; A61N 5/0613; A61N 1/32; A61N 2007/0008; A61N 2007/0017; A61N 2007/0034; A61N 2007/0047;
(Continued)

(56) References Cited

U.S. PATENT DOCUMENTS 4,286,592 A    9/1981 Chandrasekaran
4,404,460 A    9/1983 Kerr
(Continued)

OTHER PUBLICATIONS

Park et al., "The effect of heat on skin permeability", International Journal of Pharmaceutics, 2008, vol. 359, p. 94-103.
(Continued)

*Primary Examiner* — Elmer Chao
(74) *Attorney, Agent, or Firm* — Kilpatrick Townsend & Stockton LLP (57) ABSTRACT

The present disclosure relates to an electronic therapy device including automatic controlled application of energies along with feedback control using sensors for improved synergistic effects and further the device is configured to be used for longer periods of time for improved and optimal therapeutic results without causing any adverse effects, the device can be used for pain management, healing, fitness, cosmetic and topical delivery related applications and a method for performing electronic therapy using the said portable electronic device.

32 Claims, 6 Drawing Sheets

(51) Int. Cl.
*A61F 7/00* (2006.01)
*A61B 5/0205* (2006.01)
*A61B 5/026* (2006.01)
*A61B 5/107* (2006.01)
*A61B 5/00* (2006.01)
*A61N 1/00* (2006.01)
*A61M 37/00* (2006.01)
*A61F 7/02* (2006.01)

(52) U.S. Cl.
CPC .......... *A61B 5/1075* (2013.01); *A61B 5/4824* (2013.01); *A61B 5/4836* (2013.01); *A61F 7/00* (2013.01); *A61F 7/007* (2013.01); *A61N 1/00* (2013.01); *A61N 7/00* (2013.01); *G06F 19/322* (2013.01); *A61F 2007/0071* (2013.01); *A61F 2007/0075* (2013.01); *A61F 2007/0078* (2013.01); *A61F 2007/0093* (2013.01); *A61F 2007/0095* (2013.01); *A61F 2007/029* (2013.01); *A61M 37/0092* (2013.01); *A61N 2007/0008* (2013.01); *A61N 2007/0013* (2013.01); *A61N 2007/0017* (2013.01)

(58) Field of Classification Search
CPC .... A61N 2007/0013; A61N 2007/0021; A61N 2007/0026; A61N 2007/003; A61N 2007/0004
See application file for complete search history.

(56) References Cited

U.S. PATENT DOCUMENTS

| | | | |
|---|---|---|---|
| 4,736,088 | A | 4/1988 | Bart |
| 4,823,775 | A | 4/1989 | Rindt |
| 5,036,861 | A | 8/1991 | Sembrowich et al. |
| 5,076,273 | A | 12/1991 | Schoendorfer et al. |
| 5,139,023 | A | 8/1992 | Stanley et al. |
| 5,140,985 | A | 8/1992 | Schroeder et al. |
| 5,279,543 | A | 1/1994 | Glikfeld et al. |
| 5,421,816 | A | 6/1995 | Lipkovker |
| 5,658,247 | A | 8/1997 | Henley |
| 5,667,487 | A | 9/1997 | Henley |
| 5,697,896 | A | 12/1997 | McNichols et al. |
| 5,722,397 | A | 3/1998 | Eppstein |
| 5,772,397 | A | 6/1998 | Morris et al. |
| 5,833,647 | A | 11/1998 | Edwards |
| 5,860,857 | A | 1/1999 | Wasastjerna et al. |
| 5,860,957 | A | 1/1999 | Jacobsen et al. |
| 5,902,603 | A | 5/1999 | Chen et al. |
| 5,935,598 | A | 8/1999 | Sage et al. |
| 5,947,921 | A | 9/1999 | Johnson et al. |
| 5,948,012 | A | 9/1999 | Mahaffey et al. |
| 6,142,939 | A * | 11/2000 | Eppstein ............ A61B 5/14514 600/309 |
| 6,180,416 | B1 | 1/2001 | Kurnik et al. |
| 6,251,083 | B1 | 6/2001 | Yum et al. |
| 6,261,595 | B1 | 7/2001 | Stanley et al. |
| 6,334,856 | B1 | 1/2002 | Allen et al. |
| 6,527,716 | B1 * | 3/2003 | Eppstein ................ A61B 1/313 600/309 |
| 6,572,871 | B1 | 6/2003 | Church et al. |
| 6,623,457 | B1 | 9/2003 | Rosenberg |
| 6,649,886 | B1 | 11/2003 | Kleshchik |
| 6,662,044 | B2 | 12/2003 | Crawford et al. |
| 6,692,456 | B1 * | 2/2004 | Eppstein ............ A61B 10/0045 600/309 |
| 7,483,738 | B2 | 1/2009 | Tamarkin et al. |
| 7,650,177 | B2 | 1/2010 | Hoarau et al. |
| 2002/0055702 | A1 | 5/2002 | Atala et al. |
| 2002/0114827 | A1 | 8/2002 | Zhang et al. |
| 2002/0156415 | A1 | 10/2002 | Redding |
| 2003/0023151 | A1 | 1/2003 | Khalil et al. |
| 2003/0100846 | A1 | 5/2003 | Custer et al. |
| 2003/0208113 | A1 | 11/2003 | Mault et al. |
| 2003/0225360 | A1 | 12/2003 | Eppstein et al. |
| 2004/0073079 | A1 * | 4/2004 | Altshuler ............. A61B 5/6843 600/1 |
| 2005/0283110 | A1 | 12/2005 | Atala et al. |
| 2007/0083186 | A1 | 4/2007 | Carter et al. |
| 2009/0069041 | A1 | 3/2009 | Kitazoe |
| 2011/0264028 | A1 | 10/2011 | Ramdas et al. |
| 2013/0079605 | A1 | 3/2013 | Bandaru et al. |
| 2014/0244292 | A1 | 8/2014 | Rosenberg et al. |
| 2014/0343628 | A1 | 11/2014 | Kaula et al. |

OTHER PUBLICATIONS

Non-Final Office Action for U.S. Appl. No. 13/064,334, mailed on May 16, 2013, 21 pages.
Final Office Action for U.S. Appl. No. 13/064,334, mailed on Oct. 16, 2013, 19 pages.
Non-Final Office Action for U.S. Appl. No. 13/064,334, mailed on Mar. 24, 2014, 18 pages.
Final Office Action for U.S. Appl. No. 13/064,334, mailed on Aug. 12, 2014, 20 pages.
Non-Final Office Action for U.S. Appl. No. 13/428,670, mailed on Oct. 29, 2013, 16 pages.
Final Office Action for U.S. Appl. No. 13/428,670, mailed Mar. 21, 2014, 15 pages.
Non-Final Office Action for U.S. Appl. No. 13/428,670, mailed on Sep. 29, 2014, 16 pages.
International Patent Application No. PCT/US2016/015984, International Search Report and Written Opinion Received dated Apr. 18, 2016, 14 pages.

* cited by examiner

Fig. 1

Fig. 2A Integrated Design

Fig. 2B Two Piece Design

Fig. 3A Cross sectional view of applicator

Fig. 3B Cross sectional view of applicator

Fig. 3C Cross sectional view of applicator

Fig. 4A Cross sectional view of applicator

Fig. 4B Top view of transducer arrangement

Fig. 5A Cross sectional view of applicator

Fig. 5B Top view of transducer arrangement

Fig. 6A Cross sectional view of applicator

Fig. 6B Top view of transducer arrangement

Fig. 7A Cross sectional view of applicator

Fig. 7B Top view of transducer arrangement

PORTABLE ELECTRONIC THERAPY DEVICE AND THE METHOD THEREOF

RELATED APPLICATIONS

The present application is based on, and claims priority from, Indian Application No. 199/CHE/2013 filed Jan. 15, 2013, the disclosure of which is hereby incorporated by reference herein in its entirety.

FIELD OF INVENTION

The present invention discloses a portable, hand held, electronic therapy device that is capable of providing different kinds of energies like thermal (heat, cold), and ultrasound to the treatment area. More particularly the present disclosure relates to an electronic therapy device including automatic controlled application of energies along with feedback control using sensors for improved synergistic effects and further the device is configured to be used for longer periods of time for improved and optimal therapeutic results without causing any adverse effects. The device can be used for pain management, healing, fitness, cosmetic and topical delivery related applications.

BACKGROUND ART

It is well known fact that external energies such as heat, cold and ultrasound have long been used clinically for various medical benefits. Especially in the areas of pain management, cosmetics, healing and various therapy methods for humans or for the treatment of animals.

Thermal therapy, the application of heat and/or cold to a site of injury, is commonly recommended by Doctors/therapists for the treatment of musculoskeletal injuries. In addition, medical professionals are now prescribing simultaneous application of heat and cold energies for immediate relief of pain and inflammation caused due to injuries. It is well known that thermal therapy has benefits for both acute and chronic injuries. Procedures for application of thermal therapy in humans have been specifically defined based on tissue temperatures that have demonstrable beneficial effects. In humans, optimal therapeutic tissue temperatures range from 10° C. to 20° C. for cold therapy, and 30° C. to 45° C. for heat therapy.

Heat therapy commencing after injury results in increased local blood flow, decreased sensation of pain and increased tissue extensibility. The effects of heat therapy result in increased local tissue metabolic rate that may increase the rate of healing and facilitate stretching of local tissues.

Superficial heat is most widely used to treat patients experiencing pain, tension or hypermyotonicity because of its relaxing and palliative effects. These can heat large areas of skin/tissue but smaller volumes because the depth of penetration is less. It can raise the temperature of the tissue up to a depth of 1 cm to 2 cm. Superficial heat is used as an adjunct to an active exercise program and is most often used during the acute phases of treatment when the reduction of pain and inflammation are the primary goals.

The transfer of heat from the source to the treatment area is often classified into 3 general types: conduction, convection and radiation. An electric heat pad or hot pack shows conductive heating effects and widely used in various treatments. Normally this type of modality is applied for a time of 20 min to 30 min for devices that heat to an unknown temperature or heat to more than 40° C.

Electric heat pads have been in use for therapeutic medical purposes for many decades. Typically, a heating pad provides heat to various parts of the body for warming, pain relief and healing. In the prior art, heating pads have a square or rectangular shape and may include straps for wrapping and holding the pad around the treatment area or other areas where the heat is directed. Even heated clothing that covers a person's body has been developed for use in cold environments.

Application of cold therapy within the first 24 to 48 hr of injury results in decrease in pain, decrease in swelling, decrease in local blood flow, and decrease in the activity of inflammatory mediators at the site of injury. The typical benefits of cold therapy occurs with controlled temperatures between 10° C. to 20° C., and the benefits are immediate vasoconstriction with reflexive vasodilatation, decreased local metabolism and enzymatic activity, and decreased oxygen demand. Whereas reducing temperatures below 10° C., creates fibroblasts and microcirculations and also causes disturbances in lymphatic drainage. Cold decreases muscle spindle fiber activity and slows nerve conduction velocity, therefore it is often used to decrease spasticity and muscle guarding. The analgesic effects of cold result from a decreased nerve conduction velocity along pain fibers and a reduction of the muscle spindle activity responsible for mediating local muscle tone. It is usually most effective in the acute phase of treatment, though the patient can use it after physical therapy or the home exercise program to reduce pain and the inflammatory response.

Ultrasound energy delivery utilizes a piezoelectric material/crystal to transmit acoustic waves. Ultrasound energy when applied to the body produces a mechanical pressure wave through soft tissue to produce thermal and non-thermal effects. This pressure wave causes cell membrane distortion and generates microscopic bubbles in living tissues influencing tissue temperature, ion fluxes and intracellular activity. Cell membrane distortion also increases blood flow in and around the treatment area thus supplying fresh oxygen, nutrients, removing waste and increasing permeability of the skin, wherein the desired response in the particular tissue may greatly depend on ultrasound parameters such as frequency, intensity and time of exposure. Treatment with therapeutic ultrasound involves the method of stimulating tissue beneath the skin's surface using sound waves at 1 MHz or 3 MHz and at amplitude densities between 0.1 W/cm$^2$ and 3 W/cm$^2$.

When ultrasound is applied continuously, it vibrates the tissue molecules as a result of increase in kinetic energy. Tissue absorbs the produced kinetic energy and converts it to heat causing rise in tissue temperature. This also produces unstable bubbles, which collapse violently after growing to critical size under the pressure due to excessive energy accumulation. This implosion produces unstable cavities and also releases free radicals.

Ultrasound is often used as a thermal modality when treating soft tissue injuries and resultant pain; because it selectively heats structures up to 5 cm deep with only minimal increase in skin temperatures. Raising the tissue temperatures to 40° C. to 45° C. for at least 5 min using ultrasound has considerable physiological effects.

Ultrasound, when applied in pulses produces non-thermal effects and facilitates healing in the inflammatory and proliferative phase following soft tissue injury, increases local circulation because of the increased capillary density, and bone healing.

As the frequency of ultrasound increases, the attenuation (absorption, reflection and refraction of the sound) also increases. The frequency of the ultrasound waves is inversely proportional to the depth of body penetration. A 1 MHz ultrasound wave will penetrate about 3 cm to 5 cm below the skin whereas a 3 MHz ultrasound wave will only penetrate about 1 cm to 2 cm. While a low frequency means deeper penetration, using too low frequency will mean that the waves are too wide to properly move the molecules. Absorption and penetration of the ultrasound is very much dependent on collagen content of the tissue (Bone>cartilage>tendon>muscle>fat>nerve>blood).

Therapeutic ultrasound is used as a tool to improve rehabilitation, to relieve arthritis, to enhance wound healing process, to enhance drug permeation and also for cosmetic uses.

In the prior art, Kerr in U.S. Pat. No. 4,404,460 discloses a heat controlled clothing having multiple sections that are adapted to cover different areas of the human body. Electrical wires are employed which include bus wires and heater wires with circuitry controlling battery powered current flow.

Further, U.S. Pat. No. 4,736,088 issued to Bart discloses a therapeutic heating pad having a laminate structure which concentrates the flow of heat in one direction. The laminate structures in the form of a flannel material, which is held in a tubular configuration to form a muff for fomentation of a body member inserted therein.

Another specification issued to Kleshchik in U.S. Pat. No. 6,649,886 B1 discloses a highly flexible and reliable electrical heating cloth and method for providing a stable elevated temperature to an environmental site. The heating cloth consists of conductive resistive threads which are interwoven with non-conductive threads.

Another U.S. Pat. No. 5,948,012 issued to Mark V. Mahaffey discloses a cold therapy unit that includes a small portable ice chest and an electronic control unit to provide a unit which is safe to use right after surgery and has a portion which may be taken home by the patient.

Another U.S. Pat. No. 4,823,775 issued to Petrus P. M. Rindt discloses an apparatus for treating a patient with ultrasound waves comprising of a treatment head and an amplifier receiving an input signal depending on the desired intensity of the ultrasound waves and providing an electrical output signal on its output.

The devices available in the market can produce either of the energy and have their own limitations. A concern with the application of heat, especially electric heating pads, is controlling the amount of heat applied. For example, raising tissue temperatures 3° C. to 4° C. from the normal body temperature to attain physiological benefit, the source should be maintained at temperatures of 60° C. to 70° C. However prolonged exposure of high temperatures causes skin burns. The same way effective treatment with ultrasound requires use of high intensities that can not be used for longer time periods because it causes irritation and tissue damage.

In this disclosure we take advantage of these limitations and have developed a device that can produce both superficial heat and ultrasound in an efficient controlled manner to attain better physiological effect. Use of multiple energies, we believe can produce synergistic effect that is very well proven in case of ultrasound.

SUMMARY OF THE INVENTION

The present invention is about a portable and versatile electronic therapy device that consists of an applicator, a plurality of sensors and an electronic controller powered by a rechargeable battery/power source. The said device is capable of producing and applying different forms of energies when placed on the treatment area (the skin). The generated energies penetrate through the skin into the deeper layers to produce soothing and palliative effects to give the sense of relief. The present invention can give relief from various physiological implications in comparatively less time synergistically, without any side effects when compared to other available devices in market and as discussed in the prior art.

One of the major advantage of the present invention is that it uses a plurality of therapeutically effective energies in such a way that the operating parameters, such as temperature and ultrasound intensity, will be far less when compared to the products available in the market. This major feature makes it a safer gadget to use for a wide range of physiological conditions for a longer treatment session.

Such as herein disclosed is provided a portable electronic therapy device, comprising: an applicator and a controller wherein the applicator is configured for accepting at least one electrical input; a controller configured for providing the intensity, sequence, nature, and timing information for the different energies supplied to the said applicator; and the applicator comprising of plurality of transducers configured for converting input electrical energy to different forms of output energies that are transmitted to the dermal and sub-dermal layers; and a plurality of sensors disposed over the applicator configured for providing a feedback control signal to the controller.

Further herein disclosed is a method for performing electronic therapy using a portable electronic device comprising the steps of: attaching the device to the skin of the subject; inputting electrical energy from a power source; controlling the electrical energy power input using a controller; converting the electrical energy to different forms of output energy using a plurality of configured circuit blocks; and providing the intensity, sequence, nature, and timing signals for activating therapy using different energies or at least one energy through an applicator; and modifying the intensity, sequence, nature, and timing signals as per the feedback control signals from a plurality of sensors.

As per an object of the present invention, the disclosed device can be used for therapeutic purposes with/without the use of drugs.

As per another objective of the present invention the disclosed device is capable of producing heat, cold and ultrasound waves.

As per another objective of the present invention the disclosed device is configured to treat various types of body pain such as back pain, neck pain, shoulder pain, leg pain, sciatica, muscle pain, foot pain, arthritic pain, joint pain and bursitis.

As per another object of the present invention the disclosed device is configured to treat muscle spasm and strain.

As per another object of the present invention the disclosed device is configured for wound healing, tendon healing and bone healing.

As per another object of the present invention the disclosed device is configured for use in various cosmetic applications such as facial skin rejuvenation, wrinkle removal, scar removal, lipolysis, detoxification of skin cells, and as a massager.

As per another object of the present invention the disclosed device is configured for enhancement of diffusion of topically applied medicines or cosmetic compounds into the tissues beneath the skin.

It is another object of the present invention that the disclosed device is capable of producing energies in either continuous mode or in pulsed mode.

It is yet another object of the present invention wherein the device is capable of transmitting the energies to the treatment area either in continuous mode or in pulsed mode, most preferably in pulsed mode. The advantage of the present invention is that because it uses plurality of energies, the treatment area can be exposed to each energy in a systematic pulsed manner to avert any adverse effects and also to prolong the treatment time.

It is another object of the present invention to provide sensors for feedback on the patient status, enabling the controller to commence the supply of energies and also control the efficient use of the power shed by the power source/battery by optimizing the timing and use of the energies applied to the treatment area.

As an embodiment of the present invention, both the applicator and the controller are either separate or integrated together into a single piece.

As another embodiment of the present invention when the applicator and the controller are separate they are connected by either wire or wireless.

As an exemplary embodiment, the applicator is made of preferably a metal plate, or rubber, or polymer or a combination of materials acceptable for medical applications and can be in continuous contact with the treatment area.

A further embodiment of the present invention provides a housing for the disclosed device which is a thin flexible sheet made of polymer, or rubber, or resin, or textile, or thin metal, acceptable for medical applications. At least a part of the support material may have some kind of adhesive or wearable strap to attach it to the treatment area.

In another embodiment of the present invention the applicator of the device is fitted with plurality of transducers capable of producing Heat, Cold energies and Ultrasound waves. The applicator side which touches the treatment area is called applicator head.

In another embodiment of the present invention the applicator is provided with a transducer that can produce and transmit heat to raise the temperature of the treatment area above room temperature in the range of 25° C. to 40° C. The heater is made up of resistive patterns that perform as heating element.

In one of the embodiment of the present invention the resistive pattern that perform as heating element are printed on a flexible support material and then covered with the same material to give mechanical support without compromising the flexibility. Preferably silicone rubber, Kapton tape or any other polymer that doesn't affect its performance can be used as a support material.

In one of the embodiment of the present invention the applicator is provided with a transducer that is capable of reducing temperatures below room temperature in the range of 4° C. to 25° C. to produce the desired cooling effect.

In one of the embodiment of the present invention the transducer made up of peltier element that produces lower temperatures (i.e., below room temperature). Peltier element is a type of thermoelectric material that shows temperature gradient in response to applied current/voltage (referred to as peltier effect). The peltier effect is a transfer of temperature gradient from one side to the other side of the material, with consumption of electrical energy, depending on the direction of the current. Cooling effects of the peltier element depends on the direction of the current flow and the efficient transfer of heat from one side to the other side of the peltier material. A commonly used thermoelectric/peltier material is bismuth telluride.

In one of the embodiment of the present invention the applicator is provided with a transducer that is capable of producing ultrasound waves.

In one of the embodiment of the present invention, a piezoceramic crystal is used as ultrasound transducer. A piezoceramic crystal has advantage over the other piezo materials as it can produce better sympathetic oscillations, there by facilitating the optimization of entire applicator head. The preferred ultrasound frequencies used for therapeutic purposes are in the range of 0.5 MHz to 10 MHz, more preferably 0.5 MHz to 4 MHz and more preferably 1 MHZ and 3 MHZ. The ultrasound therapeutic device utilizes intensities in the range of 0.05 W/cm$^2$ to 3 W/cm$^2$ and most preferably 0.5 W/cm$^2$ to 1.5 W/cm$^2$.

In a further embodiment of the present invention there is provided a feedback control mechanism enabled by a plurality of sensors disposed over the applicator, which provides further control over the application of the different energies to the treatment area.

In one of the embodiment of the present invention the said electronic device is provided with various types of sensors that collect and send the data to the feedback control mechanism of the controller to control various parameters such as temperature, frequency, intensity, input power, time, etc., In one of the embodiment of the present invention the said applicator is also provided with sensors that collect data from the transducers and send it back to the feed back loop of the controller. For example, sensor for heater continuously measures the changes in temperatures and sends the information back to the controller, and the controller controls the fluctuations in temperature by controlling the input power to the heating element.

In one of the embodiment of the present invention the controller is equipped with all kinds of electronics such as microprocessors, voltage regulators, resistors, capacitors etc., that help in providing input voltage to the transducers.

In one of the embodiment of the present invention the therapy device is provided with a rechargeable battery and/or an adaptor.

In another embodiment a separate battery charger is provided that can be connected to the charging port of the device to recharge the power source/battery.

A further embodiment of the present invention the controller is provided with an ON/OFF button.

In one of the embodiment, the present invention is provided with different LEDs incorporated into the controller. These LEDs display various operational modes of the device such as 'ON', 'OFF' and 'Standby'. Different coloured LEDs can indicate which energy is being supplied.

In one of the embodiment of the present invention the controller is also provided with integrated timer circuitry that helps in controlling the time of energy exposure. This helps in shutting down the device once the treatment time is over and can be programmed in such a way that it won't switch ON the device unless the time gap between two treatment cycles is complete.

It is an exemplary object of the present invention, wherein the device can be used to increase the permeation of the skin to the topically applied medicament (enhanced drug delivery).

A further embodiment of the present invention there is provided a device which is having a sleek design having aesthetic features for attracting the customers.

Additional objects and the advantages of the invention will be set forth in the description which follows and in part will be obvious from the description or may be learned by the practice of the invention. The objects and the advantages of the invention may be realized and obtained by means of the instruments and combinations particularly pointed out in the appended claims.

DETAILED DESCRIPTION

The present invention is an electronic therapy device useful to treat various physiological conditions. The device consists of a controller, sensors and an applicator. The applicator consists of plurality of transducers that produce heat, cold and ultrasound energies respectively. Where as the controller consists of all the required electronics to control energies produced by transducers. The controller is configured to modify the intensity, timing etc of the different energies which are applied over the treatment area (skin) over the feedback control signal obtained from the sensors. Both the controller and the applicator are connected by either wire or wireless or can be integrated into a single product.

The available marketed products utilize high energy intensities to achieve physiological benefits. Long exposure to these energies individually at higher intensities could cause adverse effects such as; heat causes skin burns, ultrasound causes tissue irritation and damage, whereas uncontrolled cold can lead tissue damage leading to complete numbness.

The present disclosure is intended to carry out therapeutic treatment with lowest possible energy intensities to achieve a therapeutic effect. A combination of heat-ultrasound or cold-ultrasound or heat-cold-ultrasound when applied to the treatment area in a systematic manner will show synergistic effect leading to better and faster therapeutic relief.

Superficially applied heat follows a top-down heating mechanism and can heat a region of 1 cm to 2 cm depth. Ultrasound follows bottom to top heating mechanism i.e., it first heats or shows its effect on the deeper tissue (from 2 cm to 5 cm). Because of these limitations the thermal energy from these two distinct modes can only heat up a small cross sectional area of the tissue. When the same energies used in combination it is possible to treat larger cross sectional area for better physiological effects.

Cold follows a top-down cooling mechanism and can penetrate into the dermal and sub-dermal layers to show its effect. The cold transferred to the patients' skin, muscle, or tissue has several beneficial effects. Cold decrease cellular metabolism and causes vasoconstriction of the blood vessels in the area. This decreases the inflammation in the area and thus the associated pain and swelling. In combination with ultrasound it shows an additive effect.

Providing these energies in a controlled pulsatile manner, reduces the risk of adverse effects while still achieving the desired therapeutic effect.

Since larger volume of dermal and sub-dermal tissues can be exposed to the energies when used in combination, especially heat and ultrasound, there will be increased blood flow around the treatment area providing fresh oxygen and nutrients, and increasing subsequent tissue metabolism. This will help in faster tissue regeneration giving relief from pain, wound healing etc., which is not possible with products available in the market, utilising single energies. Cold decreases nerve conduction velocity thus blocking pain sensation. When used in combination with other energies it helps in reducing pain, inflammation, spasms etc.

Response of various tissue to specific energy have been observed and reported during the studies about tissue characterization. All these imply that uncontrolled exposure of tissues to the energies such as thermal energy causes physical and functional damage. The tissue damage includes, without limitation ablation, coagulation, degranulation, and desiccation. Alternatively, energy delivery in certain particular forms has also been characterized as promoting reproductive stimulation in certain tissues. Certain desired results have been disclosed with respect to intending controlled tissue treatments with thermal energy. In any event, the pronounced effects observed from tissue because of energy delivery, it is often desired to control and accurately select the localization of tissue/energy interaction in order to treat only the intended tissue, else normal surrounding tissue is affected with harmful results.

Accordingly, the different energy delivery modalities have been specifically characterized as providing particular benefits and problems versus other modalities with respect to various specific tissues and related medical conditions. The nature of the condition to be treated, as well as the anatomy of the area, can have significant impact on the desired result of energy delivery, which directly differentiates between the appropriateness or inappropriateness of each of the different energy delivery modalities for such application (as well as the corresponding particular operating parameters, systems, and methods for delivering such energy).

Depending upon the particular energy modality, various different parameters may be altered to get the required effect in particular tissues, including which type of effect is achieved (e. g. ablation, coagulation, desiccation, etc.), as well as depth or degree of the effect in surrounding tissues. In accordance with a non-limiting embodiment of the invention, pulsed heating is synchronized with pulses of pressure waves such that both pulses reach the target simultaneously. Further embodiment includes pulsed cooling synchronized with pulses of pressure waves such that both pulses reach the target simultaneously. Yet another embodiment includes pulsed heating followed by pulsed cooling and both are synchronized with pulses of pressure waves such that both pulses reach the target simultaneously. In one example, the velocity of the ultrasound wave may be about 3.0 m/sec or more, and the time of releasing the heating pulse depends on the propagation speed of the heating pulse and the respective distances of the thermal and wave devices to the target. The heat of each pulse is dissipated prior to the arrival of the subsequent heating pulse.

Figure 1:
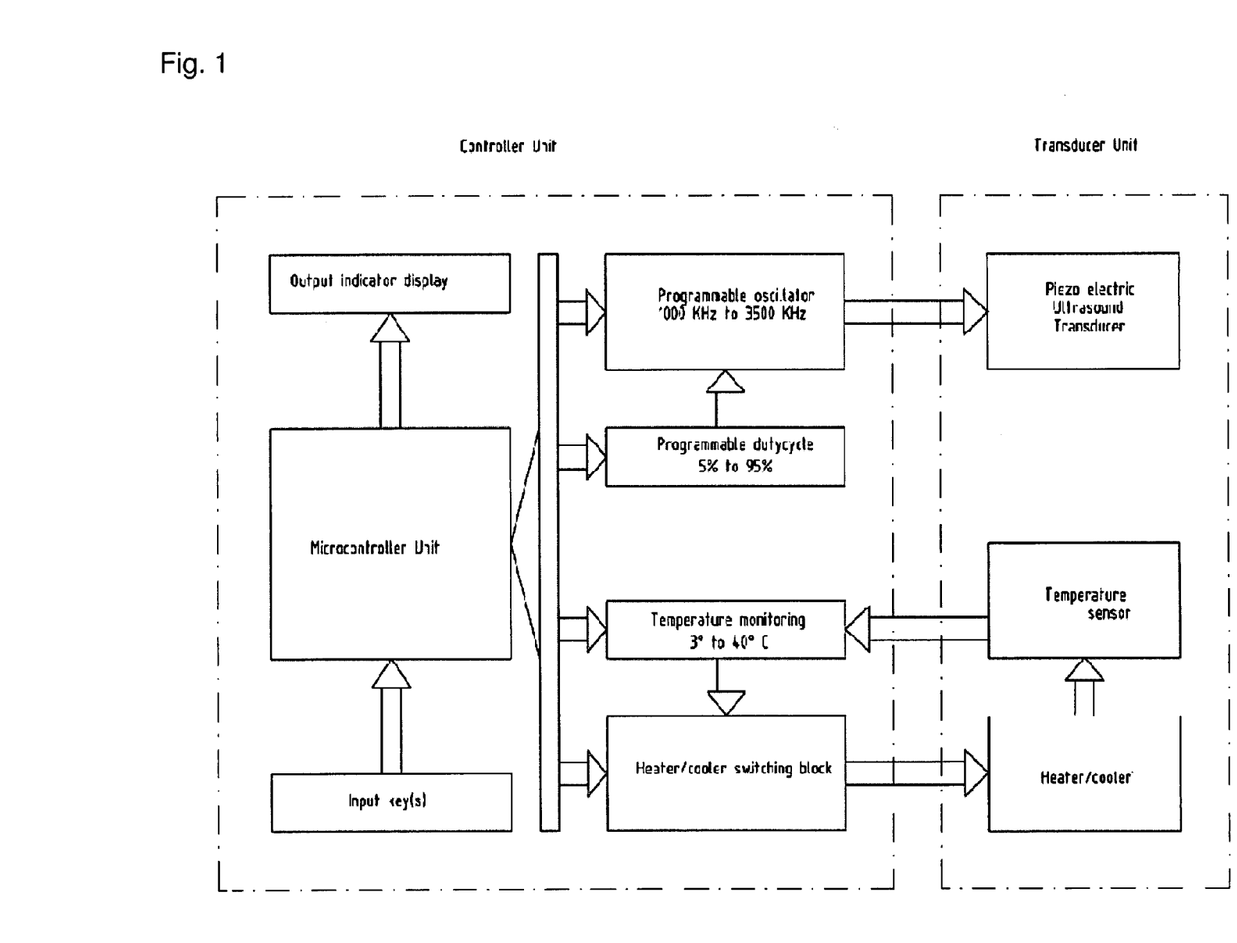
FIG. 1 illustrates the block diagram of the portable electronic therapy device

FIG. 1 shows a schematic block diagram of the proposed portable electronic therapy device. The device consists of a controller and applicator. The power is provided by a battery or capacitor of a suitable power supply unit. The controller comprises of a microprocessor unit and controls a plurality of electronic circuit modules for the generation of different energy forms like heat, cold and ultrasound. The controller as disclosed herein is programmed for the duration, switching sequence and intensity of each of these energies. The applicator consists of suitable transducers capable of delivering heat, cold and ultrasound to the skin/treatment area. The applicator also consists of plurality of sensors for the purpose of feedback and control. The sequencing of the various layers could be altered and does not necessarily have to be in the order as shown in figures.

Figure 2A:
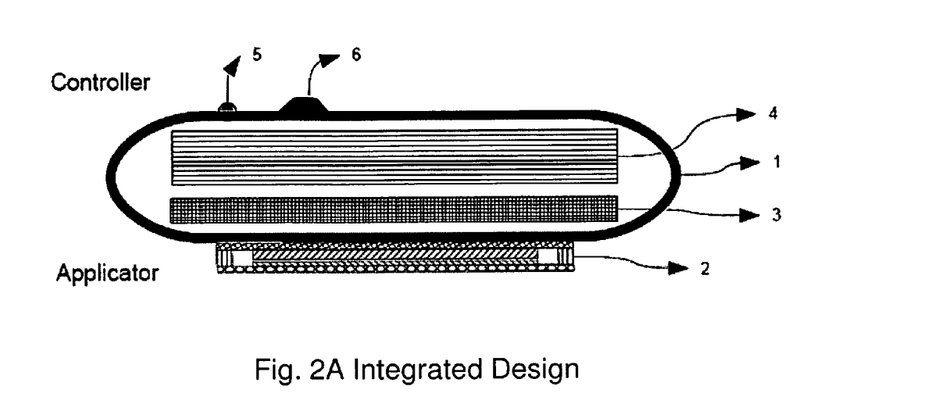
FIGS. 2A and 2B illustrate schematic cross sections of possible configurations of the electronic therapy device
Figure 2B:
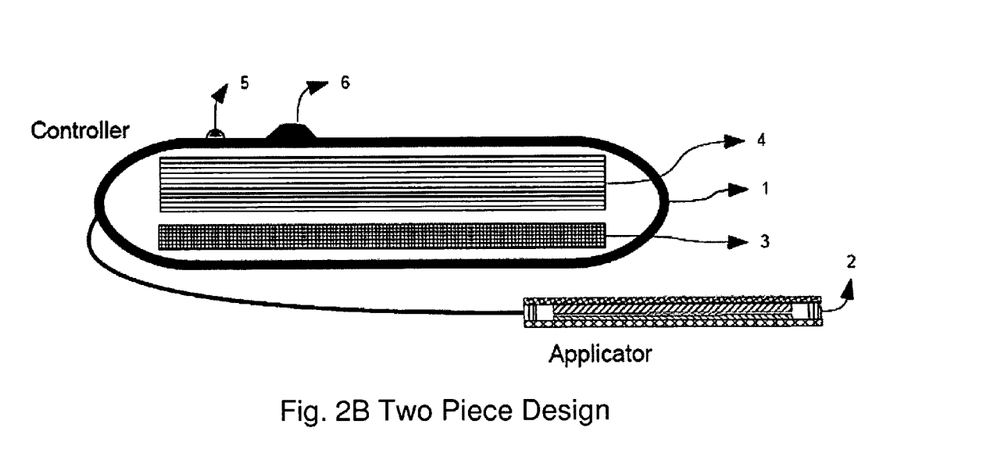
Figure 3A:
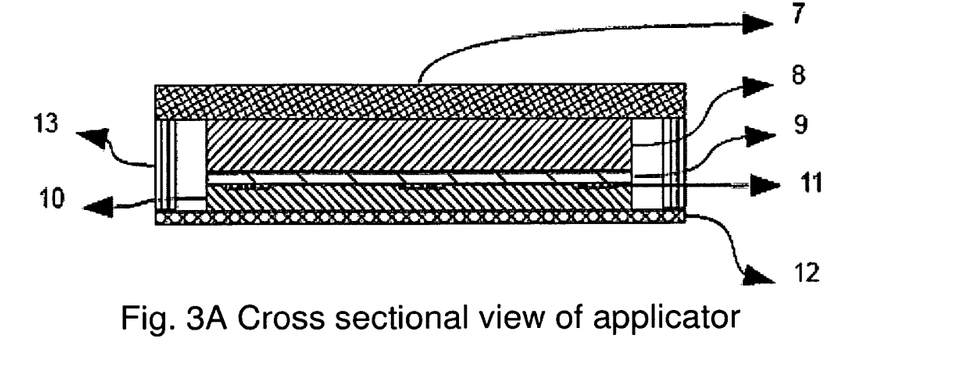
FIGS. 3A to 3C, FIGS. 4A and 4B, FIGS. 5A and 5B, FIGS. 6A and 6B, and FIGS. 7A and 7B illustrate schematic cross sections of possible applicator configurations and corresponding transducer arrangements.
Figure 3B:
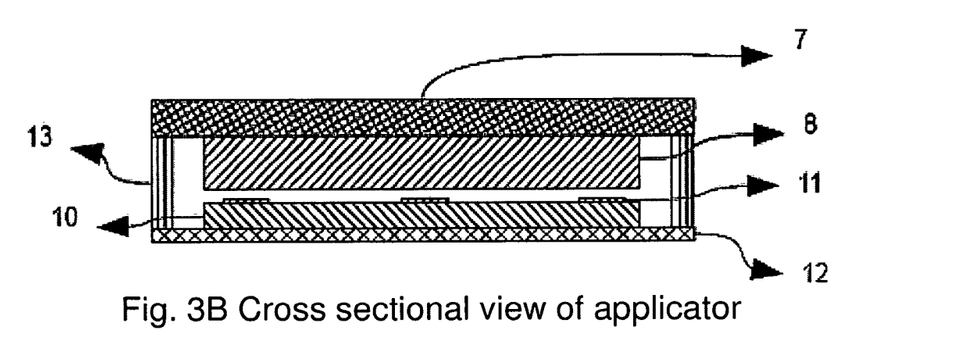
Figure 3C:
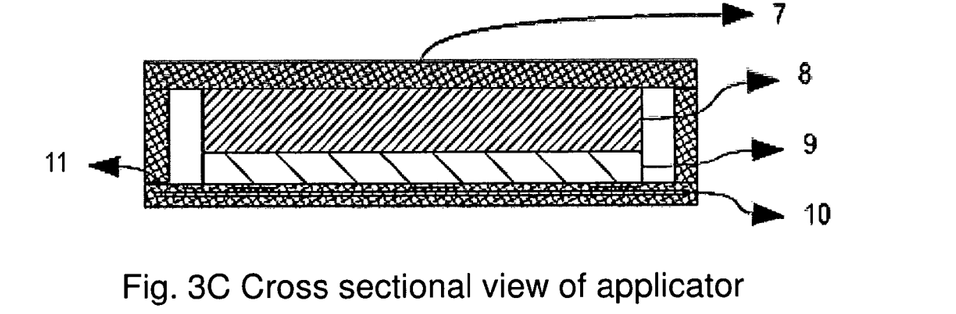
Figure 4A:
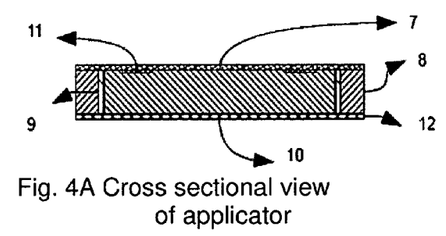
Figure 4B:
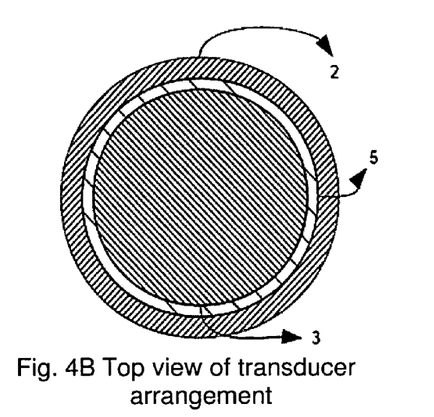
Figure 5A:
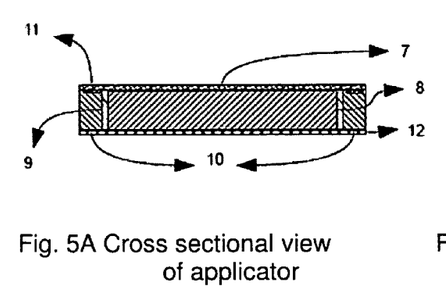
Figure 5B:
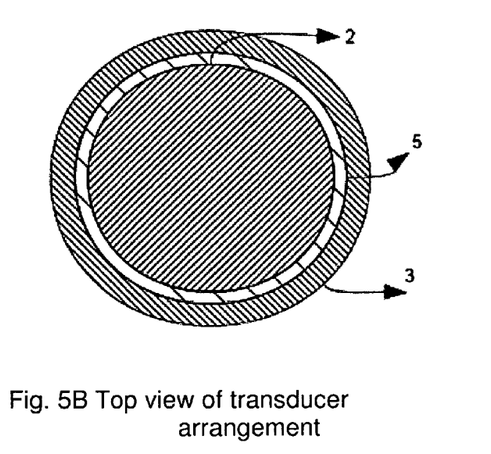
Figure 6A:
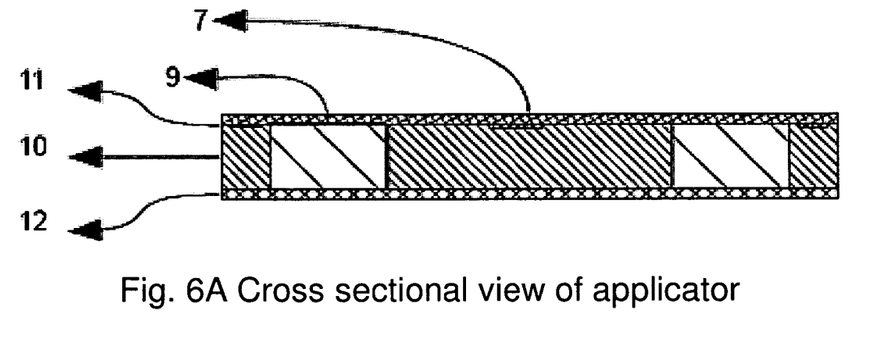
Figure 6B:
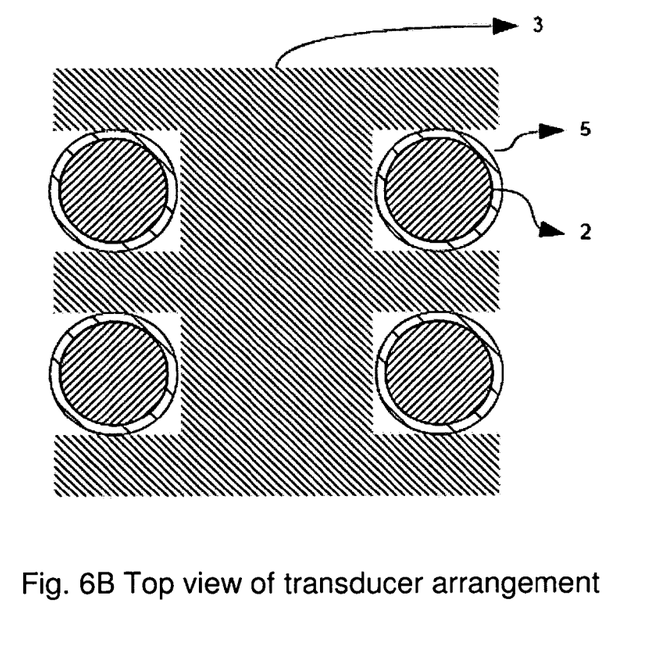
Figure 7A:
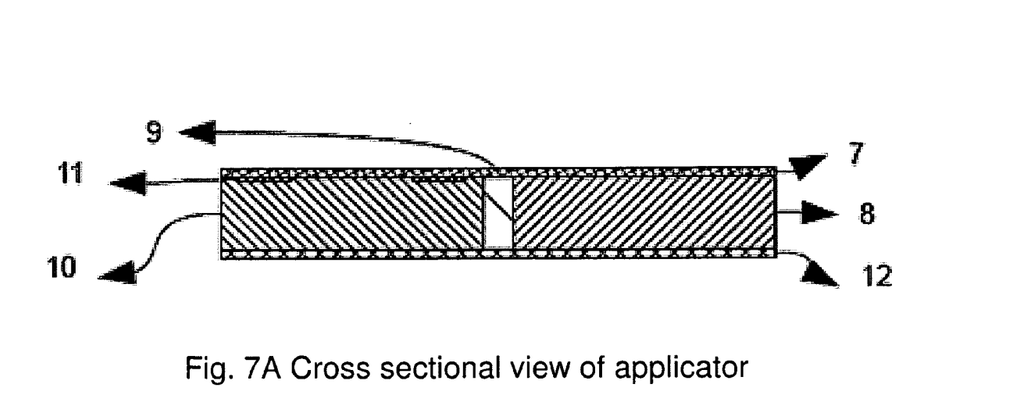
Figure 7B:
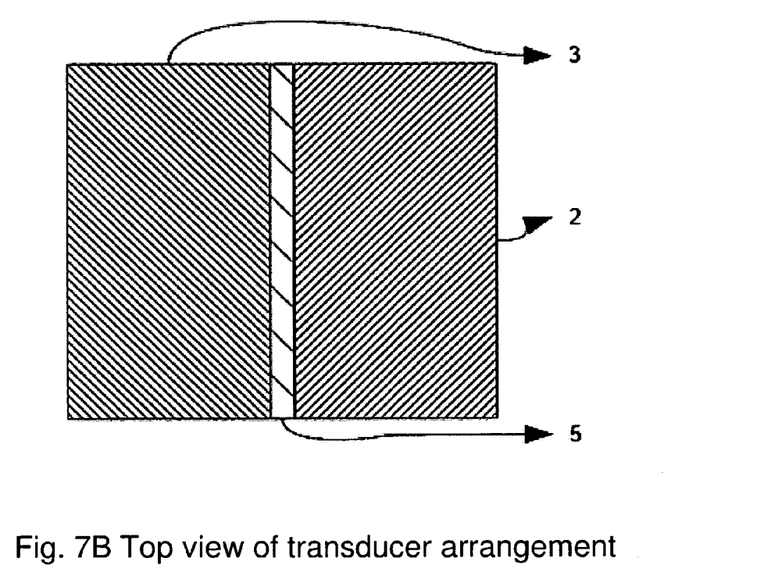

FIGS. 2A and 2B show the schematic cross sections of different possible electronic therapy device designs. Controller (1) comprises of electronic circuitry (3), rechargeable battery (4), on/off switch (6) and an LED indicator (5). FIG. 2A illustrates the integrated design where both the controller and applicator makes a single unit. Where as FIG. 2B illustrates the two piece design in which both the controller and applicator are two separate entities and are connected through a wire/wireless.

FIGS. 3A to 3C, FIGS. 4A and 4B, FIGS. 5A and 5B, FIGS. 6A and 6B, and FIGS. 7A and 7B illustrate the schematic cross sections of different possible applicator designs. The applicator usually comprises of ultrasound transducer (8), heat/cold transducer (10), insulation layer (9), temperature sensors (11), top cover (7) and bottom cover. In some of the embodiments this also consists of side support (13).

In one of the embodiment the applicator is designed in such a way that heat/cold transducer is fixed to the bottom covering (4) and the ultrasound transducer is fixed to the top covering (1) and both these are connected together with the help of side support (6).

The sequencing of the various layers and the transducer arrangement could be altered and does not necessarily have to be in the order as shown in figures. A person skilled in the art will be able to appreciate that the sequencing of the components in layered format in housing can be done in numerous ways. In an exemplary embodiment the portable electronic therapy device includes two major components: a controller and an applicator. Controller comprises of a power source and a microprocessor based controller, a plurality of electronic circuit blocks for creation and control of different energies. Applicator comprises of plurality of transducers for generation and transfer of the said energies to the skin/treatment area.

In an non limiting embodiment, the power source can be a rechargeable battery, an AC power adapter and/or a capacitor wherein the input power unit is configured for delivering current of range 0.1 mA to 1000 mA and delivering potential of range 1V to 18V DC. The said device comprises of a plurality of circuit blocks which are configured and connected to various transducers for converting the input energy to heat, cold and ultrasound. This section is provided with a switch to keep the device in on/off/standby mode to conserve energy when not in use. The standby function is optionally automated based on the program in the controller.

The controller has a microprocessor containing the required software for operation. The main function of the controller unit is to control the sequence, intensity and duration of the energy forms described earlier in association with the electronic circuit blocks which will be described in the following sections. The controller also interfaces with the detecting transducers and do the required computation for quantifying the detected values, and other related housekeeping functions. In an embodiment the various forms of energy that are supplied to the treatment area vide a combination effect of control signals the controller and the transducer supplied pulses with a minimum duration of 1 millisecond or more.

The controller is described in particular with blocks for a better understanding and in not with a view to limit its functions in any way. The controller herein described is a programmable controller and the different functionalities of the controller are preloaded. One of the electronic circuit blocks is for the generation of controlled heat or cold. This block consists of an electronic switch controlled by signals from the controller. This block also contains a subsystem that monitors the temperature and relays the same information to the controller. The controller is further configured/programmed for altering the outputs on the basis of the feedback signals provided by the sensors disposed over the said applicator. Based on the settings and the program running in the controller, the exact temperature and duration of application of heat or cold can be precisely controlled by this circuit block. This block uses a heating element and/or peltier element as a transducer. The said heating or cooling element can be printed, flexible, or of any other suitable type configured for a scale of temperatures with fixed upper and lower limits. Another transducer used by this block is a temperature sensor integrated circuit, used for the feedback mechanism. The temperature, duration and sequence are all controlled by signals from the controller. The system uses high resistance patterns or peltier element for converting electrical energy into heat energy between 25° C. and 200° C. and preferably 25° C. to 40° C., and peltier element for converting electrical energy into cold energy between 1° C. to 25° C. preferably 4° C. to 25° C. The preferred range of heat and cold temperatures could be close to the temperatures that is user/patient compliant and can be exposed to the treatment area for a longer time without the feel of discomfort.

Another circuit block that is reusable is used for the generation of ultrasonic frequency oscillations. This block takes input from the controller and generates ultrasonic frequencies in the range of 1 MHz to 3 MHz. A subsystem of this functional block amplifies the generated oscillations in a controlled manner. This circuit block uses either a piezoelectric quartz crystal/polymer/ceramic transducer to supply the ultrasonic energy to the skin/treatment area. The duration, sequence and amplitude of the output are all controlled by signals from the controller.

The Controller is provided with LED lights (red/green/yellow) to indicate various stages of the device operation modes. Red indicates the device is in 'ON' mode, green indicates the device is in "therapy" mode, yellow indicates the device is in standby mode/safe mode. All these are connected to the circuit blocks of the controller and are pre-programmed.

The applicator has an ultrasound sound transducer and heat and/or cold transducers. As shown in FIGS. 3A to 3C, 4A, 4B, 5A, 5B, 6A, 6B, 7A and 7B illustrate, these transducers are aligned one above the other preferably ultrasound transducer above the heat/cold transducer, one around the other preferably ultrasound transducer surrounding the heat/cold transducer and vice versa, side by side and some irregular designs to utilize the produced energies efficiently and treat the physiological condition very effectively.

Applicator also has temperature sensors placed on or around the heating/cooling element to measure the temperatures and send the information to the controller through feedback loop mechanism to maintain constant exposure temperatures. Applicator is also provided with both top, bottom and optional side coverings to form a compact, protective casing for the transducer and other electronics involved in the applicator. The bottom covering is in continuous contact with the treatment area and should be made of metal or silicon rubber or any other material known in the art that is capable of transmitting generated energies efficiently to the treatment area. The top covering is preferably made of metal or polymeric material to which ultrasound transducer can be fixed/attached. When attached to the side covering and bottom covering the transducer should be capable of transmitting vibrations to whole applicator and in turn to the treatment area.

As shown in the figures optionally the applicator is also provided with side covering in some of the designs to provide mechanical support and help in efficient transmitting of ultrasound vibrations.

As shown in the figures optionally the applicator is also provided with insulation material to prevent the degradation of ultrasound transducer by blocking the changes in temperature because of heat/cold transducers.

In an exemplary embodiment the method includes directing ultrasound waves at a tissue, and heating the tissue with thermal energy pulses, the thermal energy pulses synchronized to arrive at the tissue simultaneously with the ultrasound waves within a preset range, and wherein heat of each thermal energy pulse is significantly dissipated in an environment that includes the tissue before a subsequent thermal energy pulse arrives at the tissue. The deposited heat energy per pulse, the number of pulses and the repetition rate of the pulses are determined by a processor according to the temperature and the heat dissipation capability of the tissue.

According to another embodiment of the present invention, the tissue temperature is measured by a sensor in communication with the processor. The heat dissipation capacity of the tissue may be based on prior measurements of tissue properties or properties based on the assumption that the tissue is similar to known tissue properties; these properties include, but are not limited to, thermal conductivity, specific heat, coefficients of thermal convection etc.

In accordance with an embodiment of the present invention the method includes applying the ultrasound waves and the heat and cold energy pulses according to the shape of the treated tissue and the associated area thereof.

As discussed the energy is provided in the form of heat, cold and/or ultrasound and in combination thereof. Therefore the disclosed device includes elements including circuitry which can produce ultrasound waves, heat and cold with the help of ultrasound transducer/heating element/peltier element configured for delivering respective energies to the treatment area, and a controller for synchronizing the said energy pulses to arrive at the tissue simultaneously with the pressure waves within preset range, and such that effect of each energy pulse is dissipated in an environment neighboring the tissue before a subsequent energy pulse arrives at the tissue. The temperature pulses, ultrasound pulses and the timing signals can be controlled externally and internally as well using a software.

In an exemplary embodiment, the controller also includes a plurality of linked processors and a display, such as an LCD display. Other suitable displays may be provided. The controller may provide an interface that allows information be downloaded to an external device, such as a computer. Such an interface may allow the connection of interface cables, or it may be a wireless interface.

In another embodiment the device is provided with sensors configured for feedback control of the device, wherein the sensors provides control signals to the controller for the optimized and efficient use of the different energies to be applied over the treatment area thereby reducing the power usage of the power source/battery as compared with the other devices available in the market and thus enables the device for prolonged use without repeated charging.

In another embodiment, the said device is placed in a closed housing having a plurality of walls defining an interior space for accommodating the circuitry and the related electronics, the interior space having an upper opening permitting selective access to the interior space of the housing, a cover member being irremovably coupled to the housing such that the cover is for closing the upper opening of the interior space of the housing with an aesthetic shape which includes the shape of a computer mouse or any compact shape known in the art with the buttons configured for external control of the device place over the surface operable by the fingers of one hand and an applicator which includes a metal/polymer plate. In addition the applicator further includes support material which is a thin flexible sheet made of polymer, or rubber, or resin, or textile, or thin metal acceptable for medical applications and at least a part of the support material have adhesive to stick it to the skin and can be perforated. In an embodiment the device include an USB port for connecting with external computer and a display for viewing the data associated with the disclosed system and the subject. The housing also includes a strap for holding and application purposes.

In an embodiment the device is also provided with a separate battery charger and the controller is provided with a charging port to connect the battery charger to recharge the rechargeable battery of the controller.

In another non-limiting embodiment, the compact design of the disclosed device gives a patient the freedom to use this on the move, and at home reducing the clinic visits. The device can be used/placed on any part of the body and also for any ailment that will respond to these energies.

Numerous modifications may be made to the present invention, which still fall within the intended scope hereof. Thus, it should be apparent that there has been provided in accordance with the present invention a portable electronic therapy device and the method thereof that fully satisfies the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A portable electronic therapy device, comprising:
  an applicator and a controller; wherein the applicator is configured for accepting at least one electronic input;
  the controller configured for providing intensity, sequencing, nature, and timing information for different forms of output energies supplied to the applicator, wherein the controller comprises a microprocessor and memory that is preprogrammed to configure appropriate output energies based on therapy to be delivered for a particular treatment area, the information disposed on the memory of the controller; and
  the applicator comprising a plurality of transducers configured for converting input electrical energy to different forms of output energies, the plurality of transducers comprising (a) a thermal transducer for delivering heat and cold therapy, the heat therapy delivered at a temperature of 25° C. to 40° C. and the cold therapy delivered at a temperature of 4° C. to 25° C. and (b) an ultrasound transducer for delivering ultrasound waves at a frequency of 1 MHz to 3 MHz and with intensities in the range of 0.05 W/cm² to 3 W/cm², wherein the heat and cold therapy is produced by a resistive peltier element, wherein the ultrasound waves are produced by a piezo electric material, wherein the applicator transmits heat and ultrasound simultaneously, cold and ultrasound simultaneously, or a combination of heat and ultrasound simultaneously followed by cooling or vice versa to a subject's dermal and sub-dermal layers in a treatment cycle comprising a continuous treatment mode or a pulsed treatment mode having pulses of a minimum duration of one second or more; and a plurality of sensors configured for providing a feedback control signal to the controller, at least one of the plurality of sensors configured to measure change in temperature.

2. The portable electronic therapy device as claimed in claim 1, wherein the feedback control signal is configured for optimizing performance of the applicator by altering output energies delivered to the applicator based on feedback signals.

3. The portable electronic therapy device as claimed in claim 1, wherein at least a portion of the applicator is in contact with the skin.

4. The portable electronic therapy device as claimed in claim 1, wherein therapy is assisted by application of different energies in pulse mode.

5. The portable electronic therapy device as claimed in claim 1, wherein the device is configured to treat arthritis, joint pain, bursitis, muscle pain or injuries, muscle spasm or strain, soft tissue injuries, musculoskeletal injuries, back pain, joint stiffness, cold hands, rheumatism, neuralgia, inflammation, edema, ischemia, spasm, to stimulate enzyme activity and immune system, bone healing, tendon healing, or wound healing.

6. The portable electronic therapy device as claimed in claim 1, wherein the applicator comprises metal, or polymer or resin or composite material.

7. The portable electronic therapy device as claimed in claim 1, wherein the applicator is either integral part of the controller or electrically connected through wire or wireless.

8. The portable electronic therapy device as claimed in claim 1, wherein the applicator is provided with a contact system to keep the applicator in contact with the skin at the treatment area.

9. The portable electronic therapy device as claimed in claim 1, wherein the input power source comprises a rechargeable battery.

10. The portable electronic therapy device as claimed in claim 1, wherein the input power to at least one of the transducers is configured for delivering potential of range 3V to 18V DC.

11. The portable electronic therapy device as claimed in claim 1, wherein the pulse sequence and duration of pulses are optimized according to therapy requirements.

12. The portable electronic therapy device as claimed in claim 1, wherein the controller controls temperature, rate of heating, duration of heating, rate of cooling, duration of cooling, ultrasound energy, frequency, intensity, and duration.

13. The portable electronic therapy device as claimed in claim 1, wherein the controller further comprises LED status indicators.

14. The portable electronic therapy device as claimed in claim 1, wherein the memory is for the storage, recording and retrieval of data for further use.

15. The portable electronic therapy device as claimed in claim 1, wherein the device can be used for human or animal use.

16. The portable electronic therapy device as claimed in claim 1, where in the device controls a skin permeation rate of topically applied formulations or skin patches.

17. The portable electronic therapy device as claimed in claim 1, wherein the device is configured for use in connection with rejuvenation of facial and body skin, wrinkle treatment or removal, detoxification of skin cells, reduction or removal of stretch marks, treatment of contracture or scar tissues, or stimulation of lipolysis in adipose tissue.

18. A method for performing electronic therapy using a portable electronic device, comprising:

attaching the device of claim 1 to the skin of the subject;

inputting electrical energy from a power source;

controlling the electrical energy power input using the controller;

converting the electrical energy to one or more of the different forms of output energy using a plurality of configured circuit blocks, wherein the different forms of output energy comprise heat and ultrasound simultaneously, cold and ultrasound simultaneously, or a combination of heat and ultrasound simultaneously followed by cooling or vice versa, wherein heat therapy is delivered at a temperature of 25° C. to 40° C., cold therapy is delivered at a temperature of 4° C. to 25° C., and ultrasound waves are delivered at a frequency of 1 MHz to 3 MHz with intensities in the range of 0.05 W/cm² to 3 W/cm²;

providing intensity, sequence, nature, and timing signals for activating therapy through the applicator;

delivering a combination of output energies to the skin of the subject, wherein heat and cold therapy affects surface temperature of a region of skin surface up to 2 cm depth of tissue depth for the duration of contact, and wherein the ultrasound therapy affects a deeper tissue region of up to 5 cm of tissue depth for the duration of contact; and modifying the intensity, sequence, nature, and timing signals as per the feedback control signals from the plurality of sensors.

19. The method as claimed in claim 18, wherein the controller comprises a processor that is preprogrammed to configure the output energies to treat targeted areas of skin or subcutaneous tissue or bone.

20. The method as claimed in claim 18, wherein at least a portion of the applicator is in contact with the skin.

21. The method as claimed in claim 18, wherein therapy is assisted by application of the different output energies over a treatment area in pulse mode or continuous mode.

22. The method as claimed in claim 21, wherein the method is used to treat arthritis, joint pain, bursitis, muscle pain or injuries, muscle spasm or strain, soft tissue injuries, musculoskeletal injuries, back pain, joint stiffness, cold hands, rheumatism, neuralgia, inflammation, edema, ischemia, spasm, to stimulate enzyme activity and immune system, bone healing, tendon healing, or wound healing.

23. The method as claimed in claim 21, where in the device is used in combination with topically applied dosage forms.

24. The method as claimed in claim 21, wherein the method is used for rejuvenation of facial or body skin, wrinkle treatment or removal, detoxification of skin cells, reduction or removal of stretch marks, treatment of contracture or scar tissue, or stimulation of lipolysis in adipose tissue.

25. The method as claimed in claim 18, wherein the feedback control signal is configured for optimizing performance of the applicator by altering output energies delivered to the applicator based on feedback signals.

26. The portable electronic therapy device as claimed in claim 8, wherein the contact system comprises peel off adhesive or a strap.

27. The portable electronic therapy device as claimed in claim 1, wherein the ultrasound output energies are configured to penetrate through the subject's skin to up to 5 cm of tissue depth for the duration of contact.

28. The portable electronic therapy device as claimed in claim 1, wherein the thermal output energies penetrate a surface region of through the subject's skin to up to 2 cm for the duration of contact, and wherein the ultrasound output energy is configured to penetrate-into deeper tissue layers up to 5 cm for the duration of contact.

29. The method of claim 18, wherein the timing signals comprise delivery of the output energies for a minimum duration of one second or more.

30. The method of claim 18, wherein the sequence signals comprise delivery of a first output energy followed by a second output energy for a combination therapy.

31. The device of claim 1, wherein the controller delivers of a first output energy followed by a second output energy for a combination therapy.

32. A portable electronic therapy device, comprising:
an applicator and a controller; wherein the applicator is configured for accepting at least one electronic input;
the controller configured for providing intensity, sequencing, nature, and timing information for different forms of output energies supplied to the applicator, wherein the controller comprises a microprocessor and memory that is preprogrammed to configure appropriate output energies based on therapy to be delivered for a particular treatment area, the information disposed on the memory of the controller;
the applicator comprising a plurality of transducers configured for converting input electrical energy to different forms of output energies, the plurality of transducers comprising a thermal transducer for delivering heat therapy at a temperature of 25° C. to 40° C. and for delivering cold therapy at a temperature of 4° C. to 25° C. and an ultrasound transducer for delivering ultrasound waves at a frequency of 1 MHz to 3 MHz and with intensities in the range of 0.05 W/cm$^2$ to 3 W/cm$^2$,
wherein the heat and cold therapy is produced by a resistive peltier element, wherein the ultrasound waves are produced by a piezo electric material,
wherein the applicator transmits a simultaneous combination of the heat and ultrasound simultaneously, cold and ultrasound simultaneously, or a combination of heat and ultrasound simultaneously followed by cooling or vice versa to a subject's dermal and sub-dermal layers for a treatment cycle comprising a continuous treatment mode or a pulsed treatment mode having pulses with a minimum duration of one second or more, wherein the heat and cold therapy affects a surface region of skin surface to 2 cm depth of tissue depth, and wherein the ultrasound therapy affects a deeper tissue region of up to 5 cm of tissue depth; and
a plurality of sensors configured for providing a feedback control signal to the controller, at least one of the plurality of sensors configured to measure change in temperature and send temperature change information to the controller.

* * * * *